(12) United States Patent
Steen et al.

(10) Patent No.: US 8,408,207 B2
(45) Date of Patent: Apr. 2, 2013

(54) METHOD AND DEVICE FOR GAS SUPPLY DURING CARDIOPULMONARY RESUSCITATION

(75) Inventors: Stig Steen, Lund (SE); Audrius Paskevicius, Lund (SE)

(73) Assignee: Igelosa Life Science AB (SE)

( * ) Notice: Subject to any disclaimer, the term of this patent is extended or adjusted under 35 U.S.C. 154(b) by 249 days.

(21) Appl. No.: 12/866,873

(22) PCT Filed: Feb. 9, 2009

(86) PCT No.: PCT/SE2009/000074
§ 371 (c)(1), (2), (4) Date: Aug. 13, 2010

(87) PCT Pub. No.: WO2009/099380
PCT Pub. Date: Aug. 12, 2009

(65) Prior Publication Data
US 2010/0326443 A1      Dec. 30, 2010

Related U.S. Application Data

(60) Provisional application No. 61/198,745, filed on Nov. 10, 2008.

(30) Foreign Application Priority Data

Feb. 8, 2008   (SE) ...................................... 0800284

(51) Int. Cl.
*A61M 16/20* (2006.01)
(52) U.S. Cl. ................ 128/204.23; 128/205.24
(58) Field of Classification Search ............ 128/200.24, 128/204.23
See application file for complete search history.

(56) References Cited

U.S. PATENT DOCUMENTS

| | | | |
|---|---|---|---|
| 4,326,507 A | 4/1982 | Barkalow | |
| 4,397,306 A | 8/1983 | Weisfeldt et al. | |
| 5,036,847 A | 8/1991 | Boussignac et al. | |
| 5,327,887 A | 7/1994 | Nowakowski | |
| 5,377,671 A | 1/1995 | Biondi et al. | |
| 6,374,827 B1 | 4/2002 | Bowden et al. | |
| 6,604,523 B2 | 8/2003 | Lurie et al. | |
| 2005/0165334 A1 | 7/2005 | Lurie | |
| 2007/0169779 A1 * | 7/2007 | Freeman | 128/204.18 |
| 2007/0225623 A1 | 9/2007 | Freeman | |

FOREIGN PATENT DOCUMENTS

| | | | |
|---|---|---|---|
| EP | 0029352 A1 | 5/1981 | |
| EP | 0245142 A1 | 11/1987 | |

(Continued)

OTHER PUBLICATIONS

Steen et al. "Continuous Intratracheal Insufflation of Oxygen Improves the Efficacy of Mechanical Chest Compression-active Decompression CPR", Resuscitation 2004, vol. 62, p. 219-227.

*Primary Examiner* — Melanie Hand
*Assistant Examiner* — Andrew S Lo
(74) *Attorney, Agent, or Firm* — Brooks Kushman P.C.

(57) ABSTRACT

A method and device for providing ventilation gas to a patient during cardiopulmonary resuscitation. The device comprises: a gas source for supplying oxygen to the bronchi of the patient and a switch valve for initiating and terminating the gas supply. The switch valve is operated synchronous with the cardiopulmonary resuscitation cycle so that the switch valve operates with the same cycle as the cardiopulmonary resuscitation cycle but off-set in relation to the cardiopulmonary resuscitation cycle. The gas supply is initiated between 25% and 2% of the cycle time before the start of a compression stroke and is terminated between 2% and 30% of the cycle time after the start of a compression stroke. Alternatively, the gas supply is initiated between 25% and 48% of the cycle time after the termination of a compression stroke and is and terminated between 52% and 80% after the termination of a compression stroke.

29 Claims, 9 Drawing Sheets

FOREIGN PATENT DOCUMENTS

| | | |
|---|---|---|
| EP | 1820484 A2 | 8/2007 |
| SE | 521141 C2 | 10/2003 |
| WO | 9809041 A1 | 10/1989 |
| WO | 9011792 A1 | 10/1990 |
| WO | 2005046558 A1 | 5/2005 |
| WO | 2007123296 A1 | 11/2007 |

* cited by examiner

Prior Art    Fig. 6

METHOD AND DEVICE FOR GAS SUPPLY DURING CARDIOPULMONARY RESUSCITATION

This application claims the benefit of U.S. provisional application Ser. No. 61/198,745 filed Nov. 10, 2008.

AREA OF THE INVENTION

The present invention relates to a method and system for supplying ventilation gas to the lungs of a patient during cardiopulmonary resuscitation, CPR, more specifically mechanical cardiopulmonary resuscitation, mCPR.

BACKGROUND OF THE INVENTION

When a patient suffers cardiac arrest, it is required to initiate life-saving techniques as soon as possible, preferably within 8 minutes. If there is no blood flow for more than about 15 minutes, the brain and other organs will normally develop irreparable damage.

A previously known type of CPR is to manually compress the breastbone of the patient and to mechanically inflate the lungs of the patient.

A mechanical device for performing mCPR is known in Sweden under the trademark LUCAS® and is described in the documents SE 521141 and WO 2005/046558. Generally, the device comprises a piston that presses a cup shaped plate towards the sternum to compress the heart and thorax positioned there below in a compression stroke. The plate may be attached to the body of the patient, for example by means of a suction pressure inside the cup shaped plate or by means of an adhesive. When the plate is actively withdrawn, the sternum is lifted in order to forcedly expand the thorax of the patient. The movement stroke of the plate may be about 20% of the vertical distance over the thorax. The stroke cycle may be about 100 strokes/min. The active stroke may take about 0.1 seconds both down and up and there may be about 0.2 seconds of rest between each movement.

When performing mCPR with the above-mentioned device, oxygen may be supplied via a tracheal tube inserted into the trachea of the patient. The tracheal tube comprises a central channel with a diameter of about 6-10 mm and several small channels arranged in the wall of the tube. The tracheal tube may be of the Boussignac type, for example a tracheal tube included in a Boussignac Cardio Pulmonary Resuscitation System sold by VYGON, BP 7-95440 Ecouen, France under Ref 6508.70. Such a tracheal tube is for example disclosed in U.S. Pat. No. 5,036,847.

The small channels can be used for different purposes. In the present context they may be used for supplying oxygen gas to an area adjacent the bronchi of the patient. In this way, sufficient amount of oxygen is supplied to the patient and sufficient amount of carbon dioxide is removed by the volume changes developed during the thorax compression and by eliminating the "dead space" in the ventilation.

EP 0029352 A1 discloses a cardiopulmonary resuscitator comprising a reciprocatable cardiac compressor means for cyclically compressing a patient's chest and a ventilating means for inflating the patient's lungs to a benign limiting pressure such as between 10 and 60 cm of water over a period encompassing at least one and preferably three cycles of the compressor means. The resuscitator includes ventilator output control means for (i) preventing retrograde and exhale flow from the patient's lungs during the systolic portion of the cycle of the compressor means thus providing for a pressure increase in the patient's lungs due to compression of the patient's chest to a level well above that of the limiting pressure, for example to between 75 and 200 cm water, and (ii) periodically venting the patient's lungs, for example for two cycles of the compressor means.

One of the problems of CPR that needs attention is to obtain a sufficient pressure differential between the aorta and the right atrium, so that a sufficient coronary perfusion pressure is obtained, otherwise the heart will suffer permanent damage. Another problem is to obtain a low pressure in the pulmonary veins wherein blood is transported from the body and into the thorax, so that a sufficient refill of the thorax is obtained.

In an article entitle: "Continuous intratracheal insufflation of oxygen improves the efficacy of mechanical chest compression-active decompression CPR", published in Resuscitation 62 (2004), pages 219-227, the authors, Stig Steen et al, advocate that a continuous insufflation of oxygen (CIO) is superior over intermittent positive pressure ventilation (IPPV). The article shows that CIO results in an improved coronary perfusion pressure compared to IPPV.

However, there is a need for still better performance of mCPR.

SUMMARY OF THE INVENTION

Accordingly, an object of the present invention is to mitigate, alleviate or eliminate one or more of the above-identified deficiencies and disadvantages singly or in any combination.

In an aspect, there is provided a method for providing ventilation gas to a patient during a cardiopulmonary resuscitation cycle including a compression stroke and a decompression stroke of a thorax of the patient, comprising: arranging a distal end of a gas supply tube in a trachea of the patient; supplying said gas to a proximal end of said gas supply tube for delivery of said gas at the distal end of the gas supply tube; operating a switch valve for initiating and terminating the supply of gas via the gas supply tube; characterized by receiving a synchronization signal based on a cardiopulmonary resuscitation cycle; synchronizing said operation of the switch valve with said cardiopulmonary resuscitation cycle based on said synchronization signal so that the switch valve operates with the same cycle as the cardiopulmonary resuscitation cycle but off-set in relation to the cardiopulmonary resuscitation cycle.

In an embodiment, the method may comprise initiating the supply of gas based on the synchronization signal so that the gas supply is initiated between 25% and 2% of the cycle time before the start of a compression stroke.

In another embodiment, the method may comprise terminating the supply of gas based on the synchronization signal so that the gas supply is terminated between 2% and 30% of the cycle time after the start of a compression stroke.

In still another embodiment, the method may comprise initiating the supply of gas based on the synchronization signal so that the gas supply is initiated between 25% and 48% of the cycle time after the termination of a compression stroke.

In yet another embodiment, the method may comprise terminating the supply of gas based on the synchronization signal so that the gas supply is terminated between 52% and 80% after the termination of a compression stroke.

The synchronization signal may be provided by means of at least one of: a signal emitted by a mechanical cardiopulmonary resuscitation device; a pressure switch plate arranged adjacent at the patient and exposed to compression forces during a compression stroke for activation of said switch upon compression of the thorax; a gas pressure meter measuring pressure in the gas supplied to the patient, for example adjacent the distal end of the gas supply tube; a blood pressure meter measuring blood pressure in the vascular system; a gas flow meter measuring gas flow out from the lungs to the surroundings.

A valve may be operated for controlling the flow of gas out from the lungs of the patient to the surroundings via a ventilation tube for closing said valve when the supply of gas is activated.

The supply of gas may be adjusted for providing a predetermined amount of gas per cycle, for example about 50 ml.

In a further embodiment, the method may further comprise: receiving as synchronization signal a gas pressure corresponding to the gas pressure in the trachea, and determining the initiation of the compression stroke as being 2% to 15% of the cycle time before a peak maximum gas pressure or determining the termination of the compression stroke as being 2% to 15% of the cycle time before a peak minimum gas pressure.

In another aspect, there is provided a device for providing ventilation gas to a patient during a cardiopulmonary resuscitation cycle including a compression stroke and a decompression stroke of a thorax of the patient, comprising: a gas supply tube having a distal end thereof arranging in a trachea of the patient; a source of gas for supplying said gas to a proximal end of said gas supply tube for delivery of said gas at the distal end of the gas supply tube; a switch valve for initiating and terminating the supply of gas via the gas supply tube; characterized by a control device for receiving a synchronization signal based on a cardiopulmonary resuscitation cycle; wherein said device is operated for synchronizing said operation of the switch valve with said cardiopulmonary resuscitation cycle based on said synchronization signal so that the switch valve operates with the same cycle as the cardiopulmonary resuscitation cycle but off-set in relation to the cardiopulmonary resuscitation cycle.

In another embodiment, the device may further comprise at least one of the following: a device for emitting a signal by a mechanical cardiopulmonary resuscitation device; a pressure switch plate arranged adjacent at the patient and exposed to compression forces during a compression stroke for activation of said switch upon compression of the thorax; a gas pressure meter measuring pressure in the gas supplied to the patient, for example adjacent the distal end of the gas supply tube; a blood pressure meter measuring blood pressure in a vascular system of the patient; a gas flow meter measuring gas flow out from the lungs to the surroundings. A valve may be arranged for controlling the flow of gas out from the lungs of the patient to the surroundings via a ventilation tube for closing said valve when the supply of gas is activated.

BRIEF DESCRIPTION OF THE DRAWINGS

Further objects, features and advantages of the invention will appear from the following description of several embodiments of the invention with reference to the drawings, in which.

DETAILED DESCRIPTION OF EMBODIMENTS

Below, several embodiments of the invention will be described with references to the drawings. These embodiments are described in illustrating purpose in order to enable a skilled person to carry out the invention and to disclose the best mode. However, such embodiments do not limit the invention. Moreover, other combinations of the different features are possible within the scope of the invention.

Figure 1:
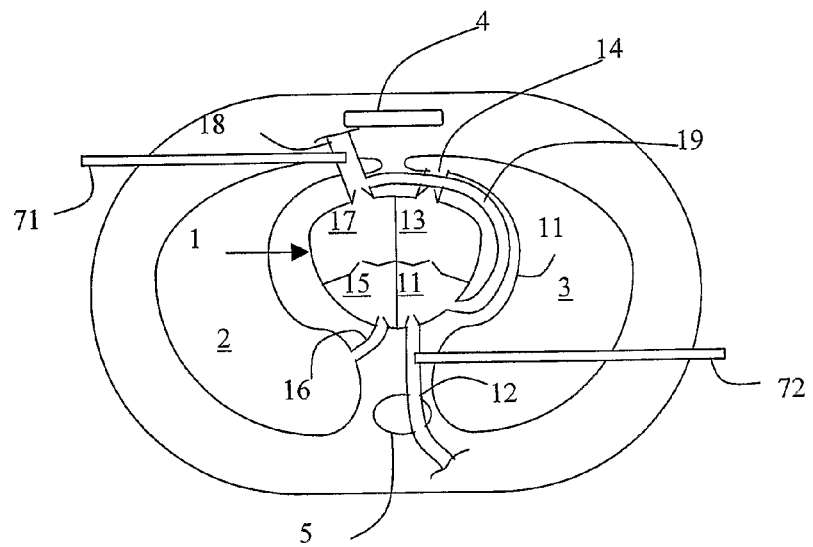
FIG. 1 is a schematic cross-sectional view of the thorax of a patient showing the heart in a horizontal section and the lungs in a vertical section.

FIG. 1 is a cross-sectional view of the thorax of a patient, comprising a heart 1 in a horizontal section and two lungs 2, 3 in a vertical section. The heart 1 is positioned between a sternum 4 and a spine 5, which are shown schematically.

The heart 1 comprises a right atrium 11 connected to the vena cava 12 and a right ventricle 13 connected to the lung arteries 14. The blood is returned from the lungs to the left atrium 15 via the lung veins 16 and is pumped out to the aorta 18 by means of the left ventricle 17. The coronary arteries 19 supply blood to the heart and extends from the aorta 18 to the right atrium 11.

Figure 2:
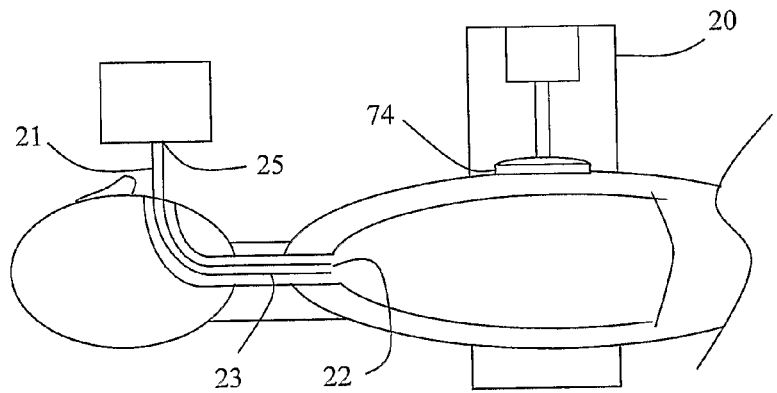
FIG. 2 is a schematic longitudinal sectional view of the patient of FIG. 1, provided with a mCPR device.

When the thorax is compressed by a mCPR device 20, see FIG. 2, substantially the same pressure exists in the right and left atriums as well as the right and left ventricles. Thus, there is no substantial pressure differential between the aorta and the right atrium, and no blood flows in the coronary arteries 19.

When the compression of the thorax is relieved, the rib bones will tend to move the sternum back to the normal position. This movement may be supported or augmented by the mCPR device as described above. The blood pressure in the thorax decreases and, thus, the pressure in the right atrium decreases simultaneously. Since the aortic valve now is closed, a pressure differential over the coronary vessels 19 is developed and oxygenated blood is supplied to the heart.

During the compression phase, some air is exhaled out of the lungs via the bronchi and trachea. During the decompression phase, some air is inhaled. However, since the frequency of compression and decompression may be about 100 strokes per minute, only small amount of air will be inhaled and exhaled, not exceeding the dead space of the bronchi and trachea. Thus, no new or fresh air is entered into the lungs, only the same air that is present in the bronchi and trachea is moved back and forth. Thus, in the prior art, a forced ventilation may be used.

Figure 3:
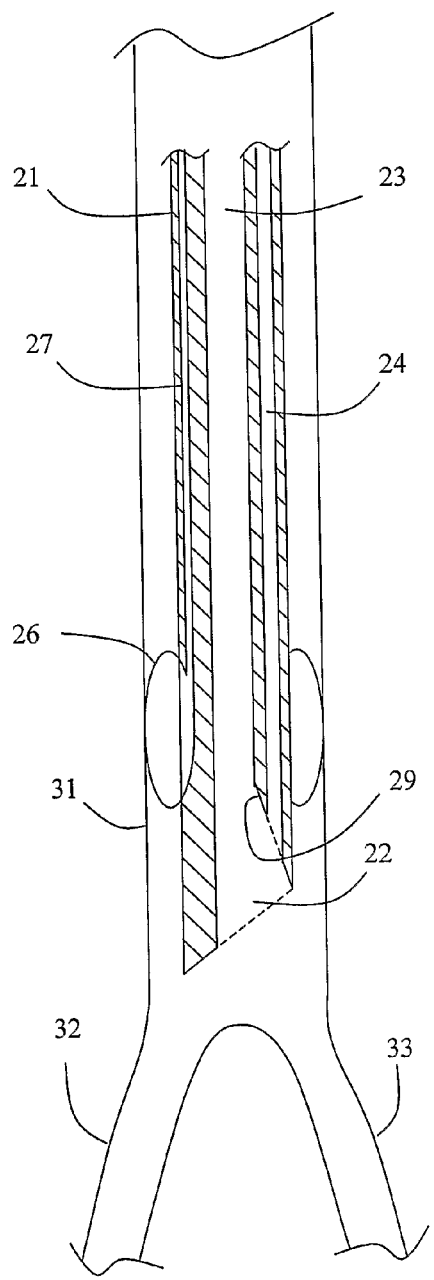
FIG. 3 is an enlarged, schematical, longitudinal sectional view of the patient of FIG. 2 showing the arrangement of the tracheal tube.

In order to circumvent the dead space and provide a sufficient amount of oxygen and a sufficient removal of carbon dioxide to the lungs, oxygen may be supplied at a distal end 22 of a gas supply tube, as shown in FIGS. 2 and 3. In this way, the dead space can be reduced and a sufficient gas balance of the patient can be achieved without the need for forced ventilation, which is separate from the mCPR device. The gas supply tube may be a tracheal tube 21, which is open to the atmosphere at the proximal end 25 and may form a flow restriction, as will be explained in greater detail below.

The tracheal tube 21 may comprise several channels as shown in FIG. 3. A first large central channel 23 connects the lungs to the surrounding atmosphere. In addition, there are several, such as four, smaller channels 24, one of which is shown in FIG. 3. These channels may be used for different purposes, such as the supply of medical agents. In the present embodiment, one or several of these channels are used for the supply of a gas, such as oxygen. Thus, the supply of gas takes place at the distal end 22 of the tracheal tube 21. In this way, the dead space is reduced.

As shown in FIG. 3, the tracheal tube 21 also comprises an expandable balloon 26 connected to a small channel 27 so that the balloon can be inflated to immobilize the tracheal tube 21 in the trachea 31 immediately above the bronchi 32, 33.

As further shown in FIG. 3, the inner side of the mouth of the tracheal tube may be chamfered 29 so that the gas channel 24 opens inside the distal end 22 of the tracheal tube.

Figure 4:
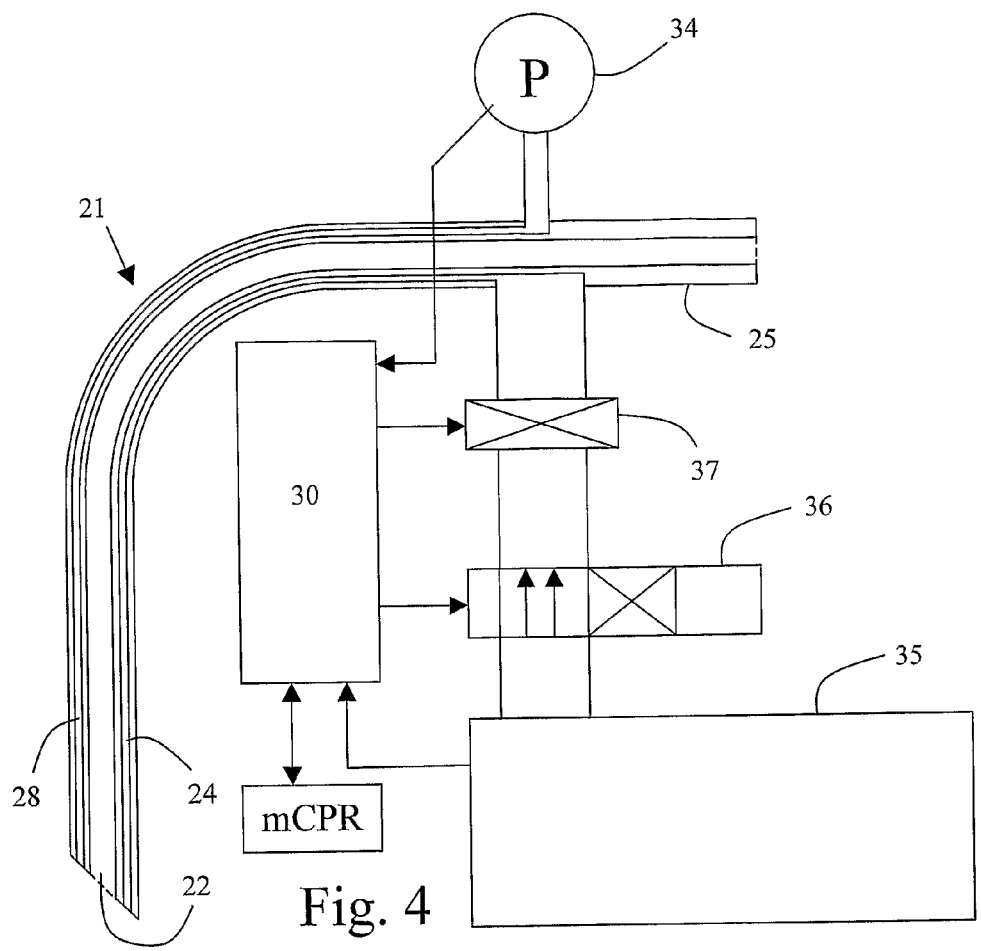
FIG. 4 is a schematic view of the tracheal tube of FIG. 3 connected to a gas supply.

Another channel 28, shown in FIG. 4, may be connected to a pressure meter 34 as shown in FIG. 4, so that the pressure at the distal end 22 of the tracheal tube can be measured.

As shown in FIG. 4, a source 35 of gas is connected to the tracheal tube 21. Gas is supplied from the gas source 35 via a switch valve 36, which is capable of initiating and stopping the supply of gas under the control of a control device, such as a computer 30 or a sequencer, which can be electrically, pneumatically or hydraulically operated. The gas then passes a flow valve 37, which essentially is a restriction or a small orifice, which passes gas at a controlled rate. The gas flow rate is adjusted to for example 30 litres per minute as described in more detail below. The flow valve 37 is connected to the proximal end 25 of the gas supply channel 24 as shown in FIG. 4.

The flow valve may form or comprise a flow meter 73, by including a flow metering device or simply by including markings of the size of the orifice opening of the flow valve 37, since the flow rate is related to the size of the opening and the driving pressure across the orifice.

Figure 6:
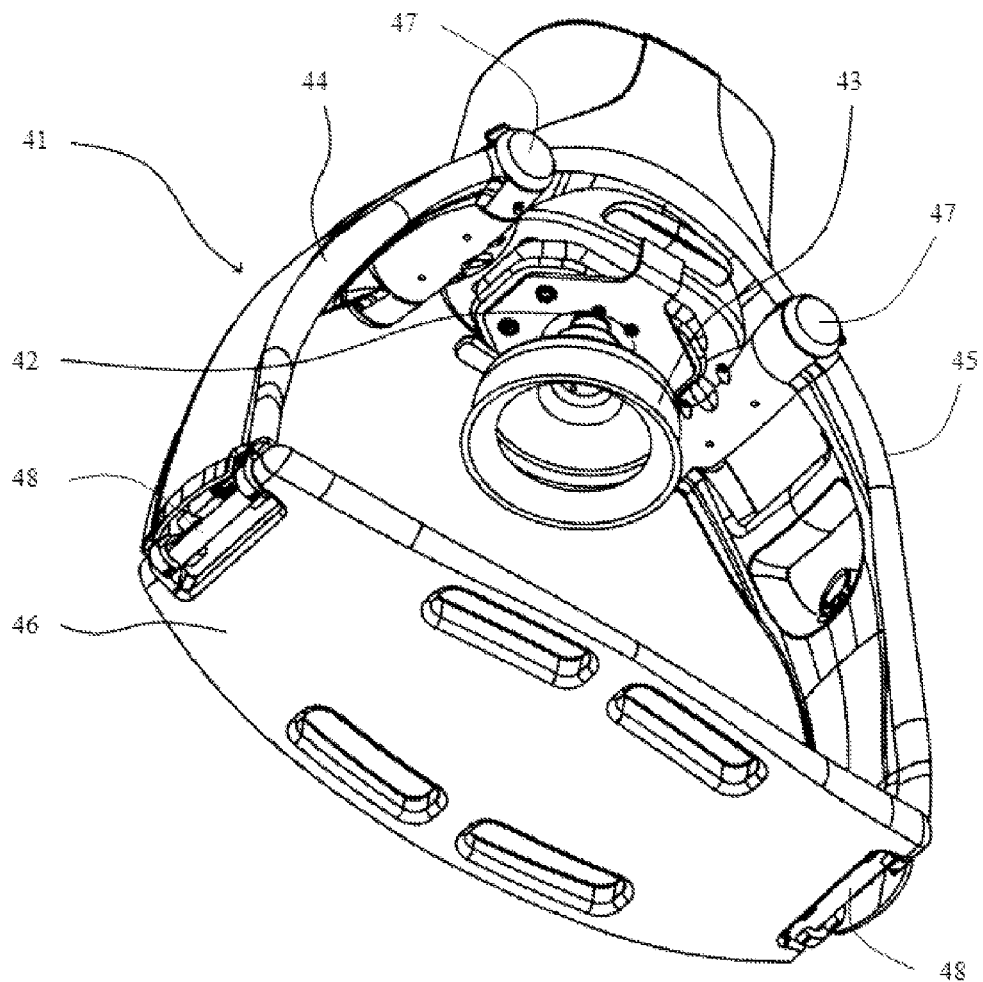
FIG. 6 is perspective view of a mCPR device.
Figure 7:
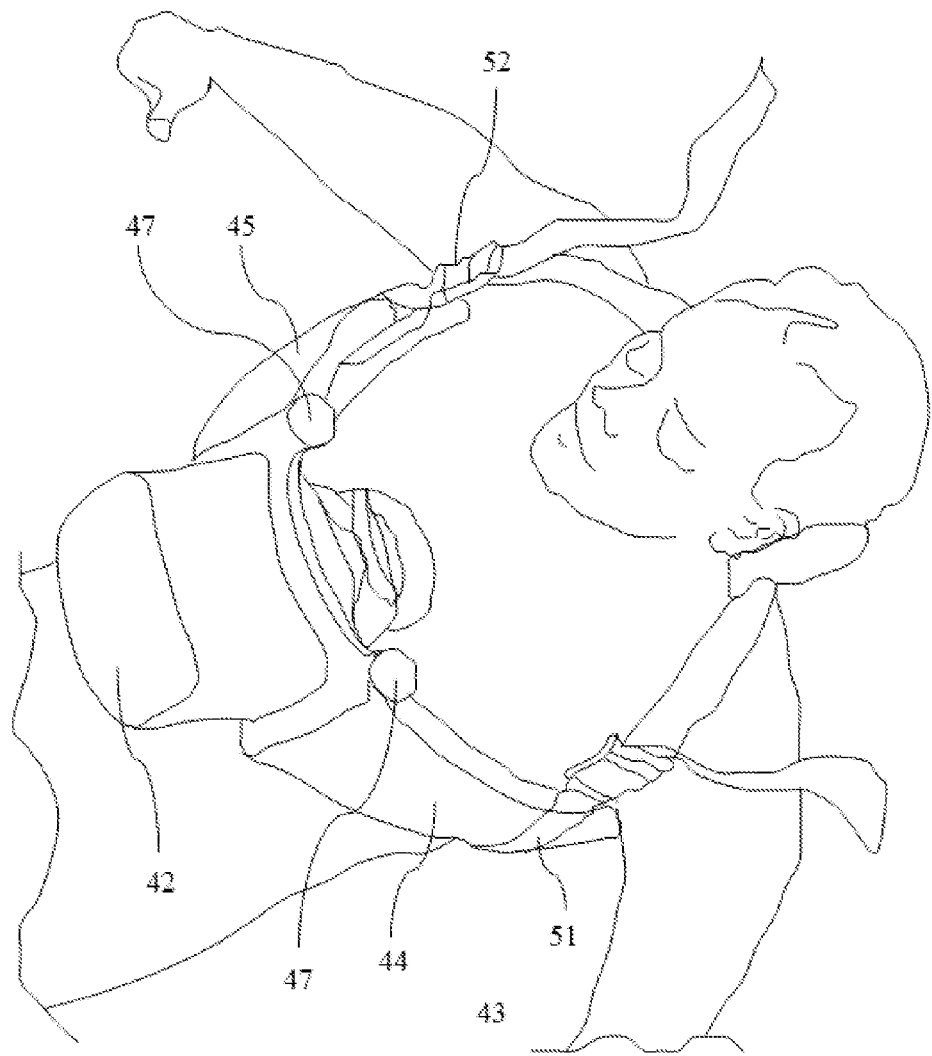
FIG. 7 is a perspective view of the mCPR device of FIG. 6 adapted on the patient.

FIGS. 6 and 7 disclose a mechanical cardiopulmonary resuscitation device according to prior art. As shown in FIG. 6, the device 41 comprises a cup shaped member 43, which is operated by a drive mechanism 42 by hydraulic, pneumatic or electric means or a combination thereof. The drive mechanism 42 is pivotably connected via swivel joints 47 to two arm members 44 and 45. The other end of each arm member is releasably and pivotably connected via swivel joints 48 to a bridge member 46. The device 41 is intended to be arranged at a patient as shown in FIG. 7, wherein a patient is shown in a supine position. The device 41 is arranged with the arm members 44, 45 extending along the side of the thorax of the patient and the bridge member 46 is arranged across the back of the patient and is not visible in FIG. 7. The cup shaped member 43 is arranged above the sternum. When the drive mechanism 42 is operated, the cup shaped member 43 compresses the thorax of the patient. The cup shaped member may be exposed to a vacuum pressure source, connecting the cup shaped member 43 to the thorax, so that the sternum is actively moved upwards during a decompression stroke. The device 41 may comprise straps 51, 52 so that the device is prevented from moving in a caudal direction However, in general, any device, including human force or activation, that can adequately change the thorax volume can be used together with the embodiments of the present invention. Activation means that the volume of the thorax is changed in any manner with the intention to perform CPR, such as by stimulation of thorax muscles, etc.

Synchronous high-pressure ventilation and negative ventilation is disclosed in the document U.S. Pat. No. 4,397,306. However, ventilation with negative pressure can be dangerous for the patient and should be avoided.

As described in the above-mentioned article, continuous supply of oxygen is preferred in the prior art because of increased coronary perfusion.

The inventors have now unexpectedly found that both coronary perfusion and mean aortic pressure and thorax refilling can be improved by providing the supply of oxygen intermittently but out of phase with the compression strokes. The supply may start before the compression stroke. Moreover, the supply may expire before the decompression stroke.

The operation of an embodiment of the invention may be as follows, see FIGS. 9 and 10 and 11.

Figure 9:
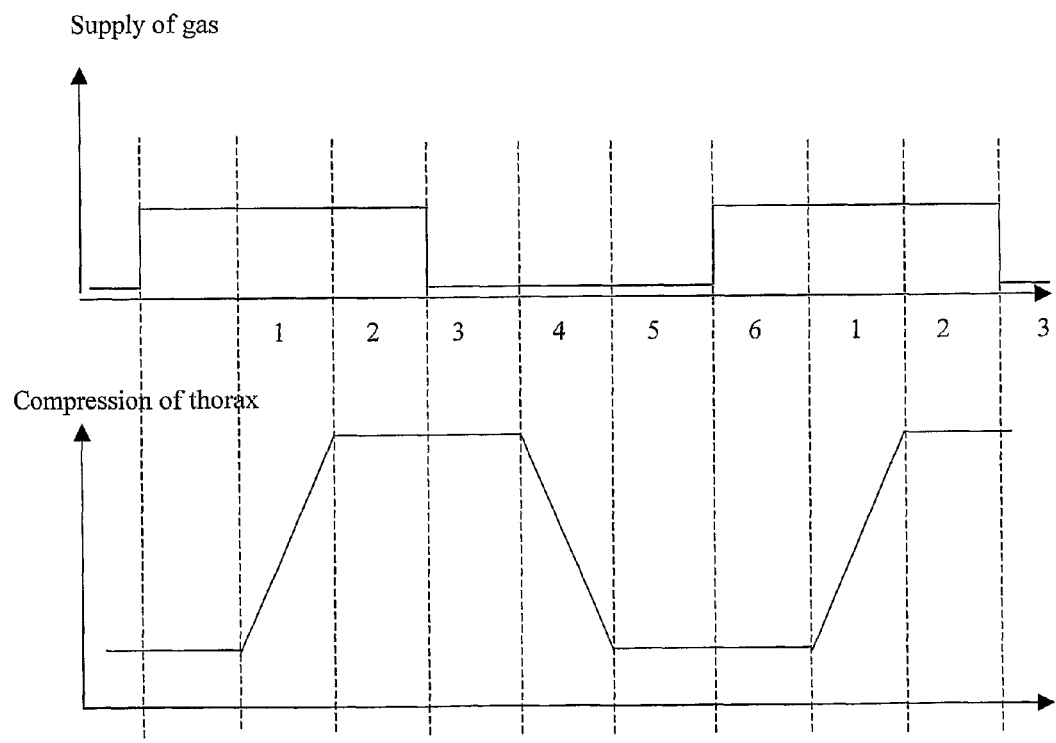
FIG. 9 is a diagram showing the timings of the supply of gas in relation to the movement of the mCPR device.

A cycle may be divided in six phases each about 0.1 seconds in duration in the embodiment as shown in FIG. 9, which shows a diagram of the supply of gas versus time and the compression of the thorax versus time.

The supply of gas is initiated before the start of phase one, whereupon a compression stroke is initiated during phase one. In phase two, the chest is compressed and the gas is still on. The supply of gas is terminated in phase three and a de-compression stroke is initiated during phase four. In phase five, the chest is decompressed and the gas is off. In phase 6, the gas is initiated and a new cycle follows.

Figure 10:
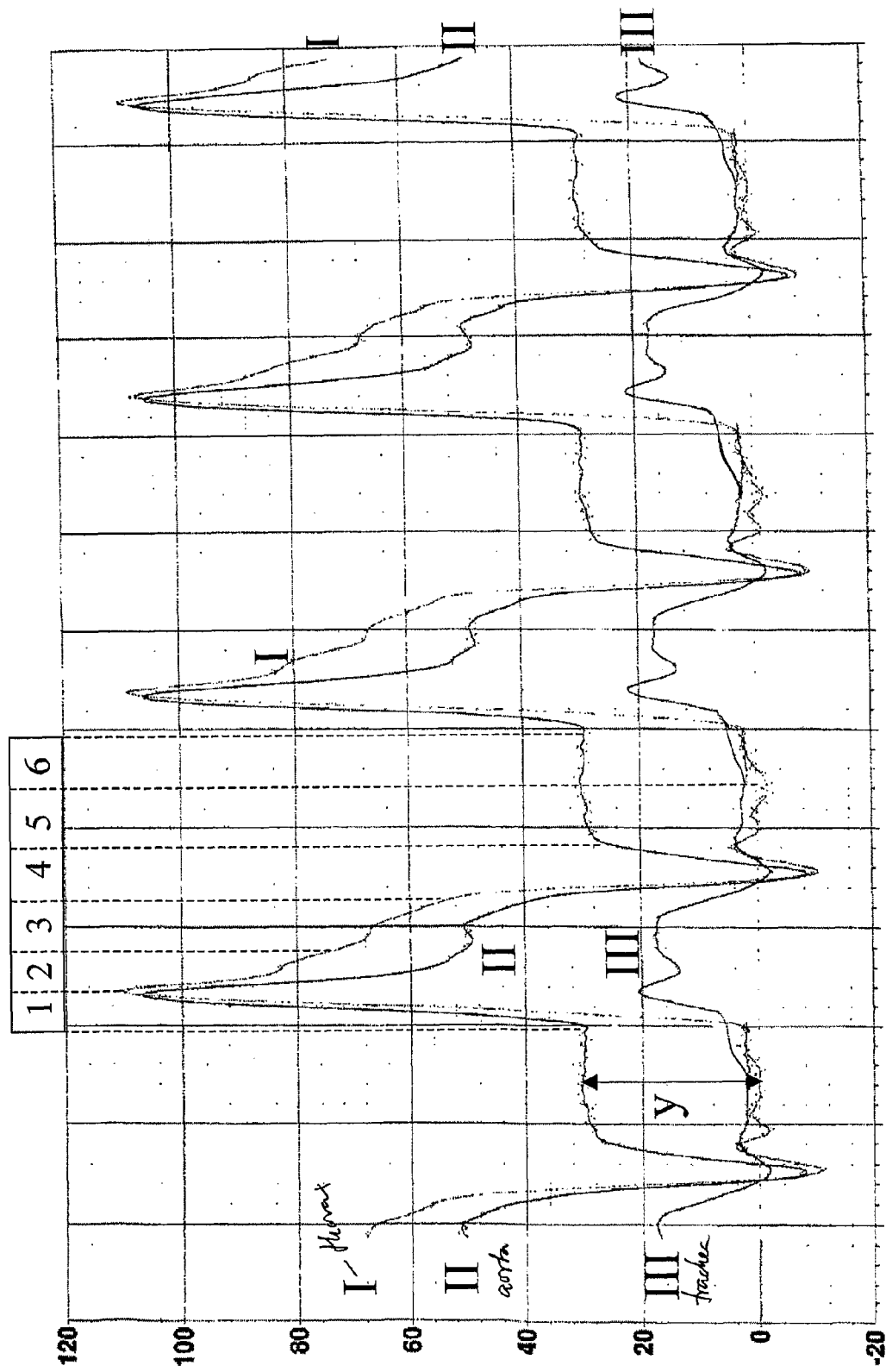
FIG. 10 is a diagram showing mCPR with intermittent supply of oxygen according to the invention.

FIG. 10 is a diagram from an experimental set-up with a pig, showing pressures at different positions in the body, viz. a first curve I showing the pressure in the right atrium 11, which is close to the liquid or blood pressure of the thorax during decompression phases, a second curve II showing the pressure in the aorta 18 and a third curve III showing the gas pressure in the trachea, i.e. essentially the reading of the pressure meter 34.

A cycle starts at the beginning of phase "1" as indicated in FIG. 10.

−1) Phase is preceded by an initiation of the gas supply, which takes place about 0.1 seconds before the initiation of a compression stroke. The tracheal pressure (III) and the thorax blood pressure (I) increases slightly and gas flows into the lungs to increase the gas volume in the lungs.

1) In phase one, a compression stroke is initiated. The compression stroke is relatively fast and takes about 0.1 seconds. During this phase, the blood pressure in the aorta and the blood pressure in the right atrium increase substantially in parallel to a peek of about 100 mmHg, as shown by curves I and II. The tracheal gas pressure also increases, as shown by curve III, resulting in an outflow of gas through the central channel 23 of the tracheal tube, which forms a restriction. Gas is still supplied via the channel 24 of the tracheal tube. During this phase, the blood pressure of the right atrium, according to curve I, is close to or even larger than the aortic pressure, according to curve II. The gas pressure in the trachea, according to curve III is almost 20 mmHg.

2) In phase two, which is about 0.1 seconds and is called "chest compressed-gas on" the pressure successively decreases in the lungs and in the aorta because gas flows out through the central channel 23 of the tracheal tube. The outflow of gas from the lungs and through the tracheal tube is partly prevented by the concomitant flow of gas through the channel 24 and out through the central channel 23 of the tracheal tube because the gas flow through channel 24 and then through the central channel 23 forms a pressure drop over the tracheal tube and possibly a Venturi effect. Thus, exhalation of gas is partly prevented by the fact that gas flow is still on during this phase. During the end of the second phase, the aortic pressure becomes constant at about 50 mmHg.

3) In phase three, the supply of gas is shut off. Thus, the pressure in the lungs may be relieved and gas flows out of the central channel 23 of the tracheal tube to decrease the gas volume in the lungs. The gas flow out through the tracheal tube decreases exponentially as the gas pressure in the lungs decreases until the pressure is almost zero, i.e. equal to the atmospheric pressure.

4) In phase four, a de-compression stroke is initiated and it takes about 0.1 seconds for the mCPR device to move the sternum to its normal position or slightly there above. Air passes inwards through the central channel 23 of the tracheal tube to the lungs, which is indicated by a negative gas pressure of the tracheal pressure reading (III). At the same time, the aortic blood pressure and the thorax blood pressure fall to below zero for a short while. The aortic pressure recoils to an aortic pressure of about 30 mmHg, because the aortic valve becomes closed preventing back-flow, while the thorax blood pressure is maintained slightly above 0 mmHg, which is the pressure that prevails in the right atrium. Thus, a coronary perfusion pressure of about 30 mmHg develops and is present for about 0.2 seconds, as shown by the arrow Y in FIG. 6.

5) In phase five, which is about 0.1 seconds and is called "chest decompressed, gas off", the blood pressure in the thorax is close to zero. The gas pressure in the lungs will not be negative or only slightly negative during a short period, because of the lifting of the sternum by the mCPR device, mainly during phase four. During the time when the thorax blood pressure is close to zero, the thorax blood vessels will be replenished with venous blood from the vena cava. The systemic venous blood pressure is a few mmHg and the blood will flow from vena cava, through the right atrium and the right ventricle to the thoracic aorta and thence to the thorax blood vessels in order to fill the thorax with blood to be oxygenated and to release its contents of carbon dioxide in the alveoli of the lungs.

6) In phase six, the gas supply is initiated in order provide a predetermined volume of gas into the lungs before the compression starts.

Then, a new cycle is started.

There are several conditions that should be considered, separately or in any combination, in order to achieve a good performance.

A) In order to supply oxygenated blood to the coronary blood vessels of the heart, it is important that the coronary perfusion pressure Y is as large as possible during as large time period as possible.

B) In order to refill the thorax with blood, it important that the blood pressure in the thorax is low during phase four, five and six, because the blood returned from the body via vena cava can then flow into the heart and the thorax. As shown by curve I, the thorax blood pressure is close to zero.

C) In order to supply the body and organs with oxygenated blood, it is important that the peak aortic pressure is large and that the surface under the aortic pressure curve II is large, because this surface is proportional to the blood flow passing to the body via the aorta.

D) The peak gas pressure in the trachea should not exceed about 30 mmHg, since this may result in haemorrhage in the lungs and oedema. The lowest pressure in the trachea should not decrease below zero for a substantial time.

Figure 11:
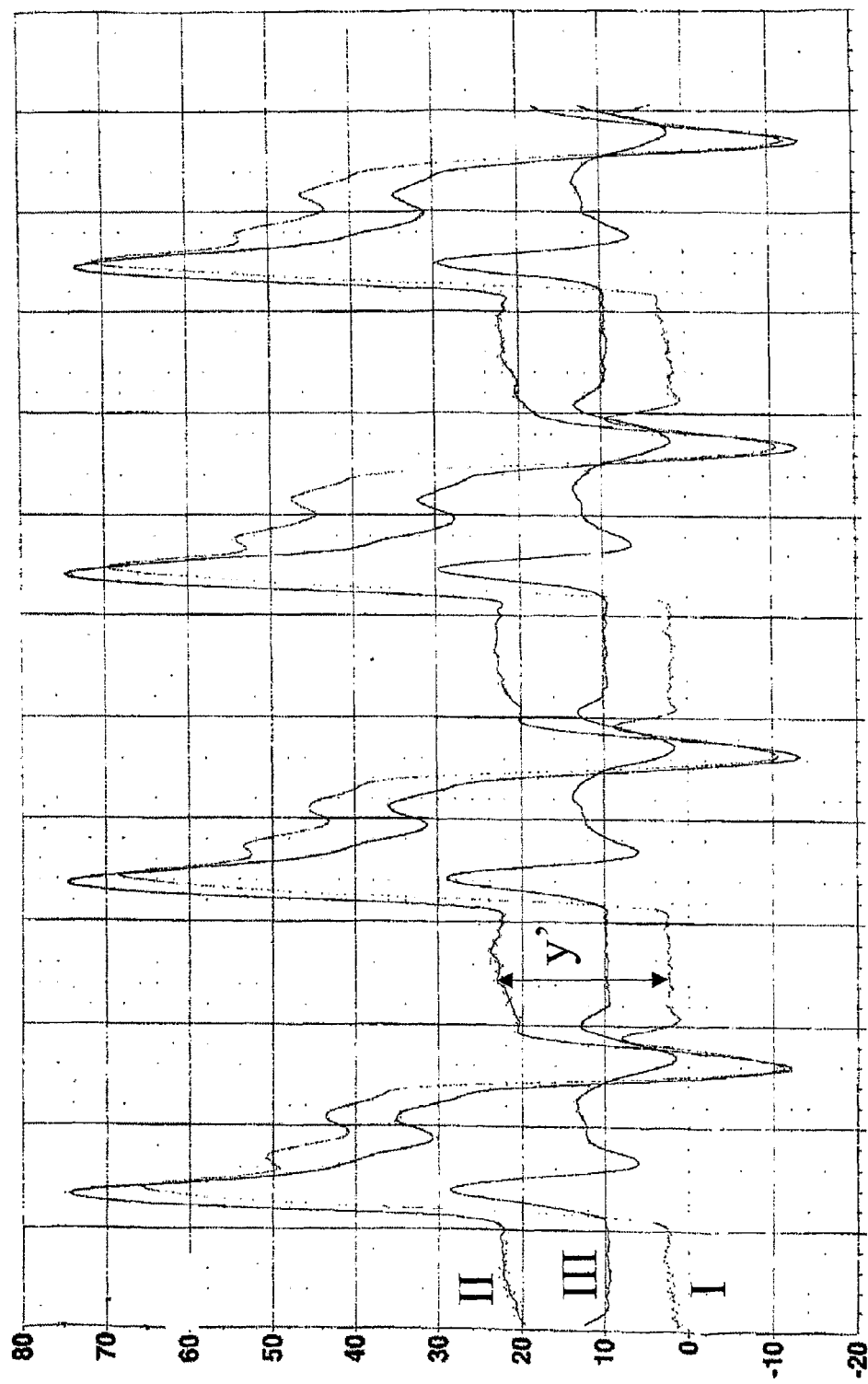
FIG. 11 is a diagram showing mCPR with continuous supply of oxygen according to a prior art CIO system.

FIG. 11 shows curves similar to FIG. 10 for a prior art system using Continuous Insufflation of Oxygen, CIO. All other conditions are the same. However, as can be seen from the curves, the peak aortic pressure is about 75 mmHg (compared to 110 mmHg), and the coronary perfusion pressure is only about 20 mmHg (compared to 30 mmHg). The aortic pressure in the fifth phase is only about 22 mmHg (compared to 30 mmHg). The peak tracheal gas pressure in the second phase is about 30 mmHg (compared to 20 mmHg).

Thus, the embodiment shown in FIG. 10 is superior and safer compared to the prior art embodiment shown in FIG. 11.

The supply of gas may be oxygen. However, in other embodiments, the supply of oxygen may be replaced by a supply of any suitable mixture of gases, such as normal air, or air augmented by oxygen, or any gas mixture.

The gas may include a therapeutic agent or pharmaca. The agent may be nebulized in the gas. Such agents may comprise hydrogensulphate, epinephrine, adrenaline, norepinephrine, noradrenalin, amiodarone, cordarone, lidocaine, ketamine, nitrous oxide, etc. Such agent may also be delivered via a separate channel.

The mechanical cardiopulmonary resuscitation mCPR can be performed without active decompression, so that the normal decompression by means of the rib-bones and the resiliency of the thorax can take place. Also manual compression can be used.

The length of the different phases can be different from that described above.

Phase six can be between 0.01 and 0.2 seconds depending on how efficiently the lungs are filled with gas. The importance of phase one is that the lungs should be filled with a sufficient amount of gas so that they exert a sufficient counter pressure towards the heart and thorax during the compression stroke. The gas supply should take place as late as possible in order to give the thorax ample time to be refilled.

Another consideration is that a sufficient amount of oxygen should be supplied so that the blood in the lungs can be sufficiently oxygenated. It has been found that an average supply of about 15 litres per minute of oxygen is sufficient for the oxygenation purpose.

Since oxygen is supplied during half of the cycle, the supply would be 30 l/min, which corresponds to 50 ml per 0.1 seconds. Since air enters the lungs essentially only during phase six, the lungs will be supplied with about 50 ml per cycle. Since there are about 100 cycles per minute, and since the normal breathing rate is about 10 per minute, this corresponds to an inhalation of about 0.5 litre per normal breathing. If only oxygen is supplied, this is a sufficient amount for oxygenating the blood in the lungs, even if account is taken to the fact that a dead space of up to 25 ml may prevail in the bronchi.

The supply of gas will introduce gas into the lungs, which is believed to augment the peak aortic pressure (II) during the following phase one and phase two. Thus, it is an advantage to introduce a large amount of gas during phase six. However, the amount of gas introduced should not be too large, compare below. It has been found that a good balance may be achieved if phase six has a duration of about 0.1 seconds and the gas supply is about 30 l/min. Since the tracheal tube is open to atmosphere at the proximal end 25, a portion of the gas supplied will pass out to the atmosphere. However, a considerable amount of the gas supplied will be delivered to the lungs, if the pressure in the lungs is sufficiently low. Moreover, the gas is delivered via a channel 24 having a small cross-sectional area, which means that the gas supplied has a considerable velocity in the direction towards the lungs.

Since gas is supplied also during phase one and phase two, gas in the bronchi will be prevented from passing out to the surrounding atmosphere during phase one and two, as explained above. Moreover, the tracheal tube will be filled with the gas, which may be oxygen. Thus, the tracheal tube will not contribute to the dead space, but it can be considered that the distal end of the tracheal tube is directly connected to the atmosphere without a dead space.

There are essentially two mechanisms by which oxygen is supplied to the lungs and carbon dioxide is removed from the lungs.

The flow of gas (oxygen) into and out of the lungs will convect carbon dioxide in one direction (out) and oxygen in the other direction (in).

Any carbon dioxide in the lungs will also diffuse from the lungs to the bronchi and the tracheal tube because of any concentration differential. If only oxygen is present at the distal end of the tracheal tube, there is a large concentration differential of carbon dioxide, resulting in a substantial transport of carbon dioxide out of the lungs, even without any gas flow. In the same way, oxygen will be transported to the lungs by diffusion if a concentration differential exists.

In order to reduce the dead space, the tracheal tube should be arranged close to the carina or connection between the bronchi such as 1-3 cm there above. In another embodiment, the tracheal tube may include tube portions partly extending into the bronchi, while the balloon immobilizing the tracheal catheter is arranged in the trachea.

Figure 14:
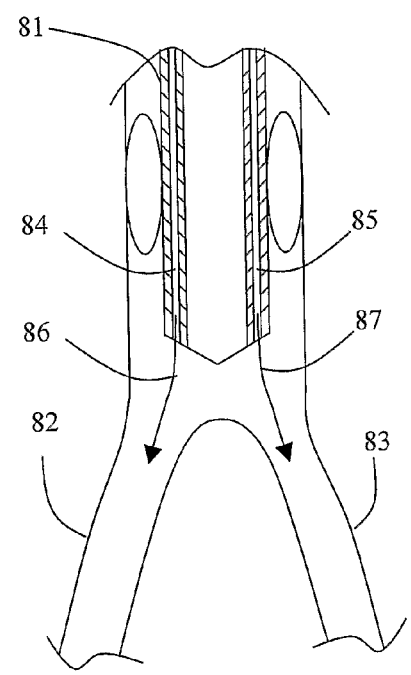
FIG. 14 is an alternative embodiment of the tracheal tube.

As shown in FIG. 14, the tracheal tube 81 may be arranged with two channels 84 and 85 for gas supply, opening towards the bronchi 82 and 83. The gas emitted from the orifice of each channel will have a substantial velocity in the direction towards the corresponding bronchi as shown by arrows 86 and 87. Thus, the gas will more easily enter the bronchi and the lungs, in order to fill the lungs with gas during phase six.

It is of no importance how the tracheal tube extends above the distal end 22 and the balloon 26. Thus, the tracheal tube may be introduced through the mouth, through the nose and pass the vocal cords, or through a hole arranged in the pharynx.

In another embodiment, the tracheal tube may be a conventional tracheal tube having only a central channel and a channel for expanding the balloon. In this case, gas (oxygen) may be supplied to the distal end of the tracheal tube by a small separate gas tube placed inside the central channel. The gas tube should open shortly before the distal end of the tracheal tube, inside the tracheal tube.

In still another embodiment, there is no tracheal tube. Instead, a gas supply tube is inserted in the trachea as far as possible so that the distal end of the gas supply tube opens at a position just above the connection between the trachea and the bronchi, which is shown in FIG. 2, wherein tube 21 is a single lumen tube, possibly with a second lumen for a pressure meter. Gas is supplied to the proximal end of the gas supply tube for the inhalation of gas and the trachea is used for exhalation of gas. The gas supply tube may comprise markings at positions corresponding to the length of the trachea of a normal person. When the gas supply tube has been inserted to the marking, the user knows that the distal end is positioned close to the bronchi as required. Since substantially no inhalation takes place via the trachea, the dead volume of the trachea is removed. The gas supply tube may end with two nozzles directed slightly sideways, as shown in FIG. 14, in order to further promote rapid inhalation of gas.

Some gas is removed from the lungs during phases one and two when the pressure in the thorax is high and when "gas is on". However, most of the gas is removed during phase three, see below. It is of importance that a sufficient amount of gas is removed before phase four, de-compression, so that the pressure in the lungs may decrease towards zero before the thorax is recoiling, either spontaneously or by active decompression. A zero pressure in the lungs during phase four and five, and most of the following phase six, will ensure a high perfusion pressure over the coronary vessels, as indicated by the arrow Y in FIG. 10. In addition, since the systemic venous pressure is only a few mmHg, such as below 10 mmHg, the thorax will be replenished with venous blood only if the thorax blood pressure is almost zero. Thus, it is important to keep the low thorax pressure as low as possible, which results in a limitation of the amount of gas that can be supplied during phase one. If too much gas is supplied, the low pressure will be higher if such supplied gas cannot be removed to a sufficient degree during phase one, phase two and phase three.

If a larger amount of gas is desired, the phase six can be made longer, such as up to about 0.2 seconds. Alternatively or additionally, the gas supply rate can be increased. The more gas that enters the lungs before the compression stroke, the higher will be the aortic pressure during the compression stroke. The high aortic pressure will be averaged by the blood circulation system outside the heart, such as the blood circulating to the large organs and the brain. The top pressure may be about 100 mmHg as shown in FIG. 10. On the other hand too much gas can fail to be exhaled during later phases, distending the lungs and preventing the venous return. For further alternatives, see below. The supply of gas during phase six may be between 30 ml to 70 ml, such as between 40 ml to 60 ml, for example 50 ml. The supply of gas is also dependent on the cycle time, a high cycle time may give ample time for supply of more gas during phase one.

Phase one is about 0.1 seconds and should be as fast as the conditions allows. If the compression rate is too slow, the top pressure will be lower. However, phase one should not be so short that the thorax and internal organs are damaged. The stroke of the compression phase may be about 20% of the anterior-posterior thorax diameter so that the thorax is substantially compressed. The stroke should not be so large that the thorax and the heart are compressed excessively, but be so large that the blood in the thorax is substantially moved out of the heart into the aorta.

Phase two or "chest compressed, gas on", could be between 0.1 and 0.3 seconds. This phase is for moving blood out of the heart and thorax.

There are two reasons for the blood to pass out to the aorta, physical compression of the heart, resulting in a cardiac-pump-mechanism, and increased hydrostatic pressure in the thorax, resulting a thorax-pump-mechanism.

In order for both mechanisms to be efficient, it is required that the thorax is replenished with blood during the decompression phases, as is further discussed below.

It is noted, that certain mammals do not have the cardiac-pump-mechanism, but only the thorax-pump-mechanism, such as a pig. It is believed that both mechanisms are in use in a human.

Phase three is for exhaling gas from the lungs. By shutting off the supply of gases, the gas pressure in the trachea is reduced and the gas in the lungs can be exhaled, which ensures better venous return and thorax filling during next phases. Phase three is between 0.02 and 0.2 seconds to allow the volume of gas in the lungs to decrease before the next phase. The same amount of gas, which is inhaled during phase six should be exhaled during phase three, such as about 50 ml.

Phase four should be as short as possible. By using active decompression, the decrease of the pressure in the lungs can be large. However, the pressure in the lungs should not be substantially below zero for extended time periods. When the pressure in the thorax decreases towards zero, the pressure in the left ventricle will also be lowered and the blood will tend to flow into the left ventricle via the aortic valve. However, the aortic valve is closed and will prevent such flow. Venous blood from vena cava will start to enter the left atrium, left ventricle and pass into the thorax and lungs for oxygenation.

During phase four and phase five, the left and right atriums would have a low pressure and will be filled with blood from the circulatory system via vena cava and from the lung veins, respectively. Blood will also flow from the atrium to the ventricle at each side of the heart.

During phase five and the following phase six, a considerable pressure differential is present between the aorta and the right atrium, which will result in a perfusion of the coronary arteries, thus supplying the heart with oxygenated blood.

Phase five or "chest decompressed, gas off" can be from about 0.05 sec to about 0.2 sec.

To summarize, by initiating a gas supply before the compression stroke, the top pressure in the aorta will be augmented. Moreover, the volume flow of blood out of the heart to the aorta will be larger.

Moreover, by stopping the supply of gas before the decompression stroke, the gas volume in the lungs will be lowered, resulting in a low pressure in the thorax/lungs and a fast refilling of the thorax via vena cava. In addition, the coronary perfusion pressure will be large.

Refilling of the thorax is slightly decreased during phase six, when gas is supplied to the lungs, because the thorax/lung pressure increases slightly. Since the venous return pressure is low, any increase in the thorax/lung pressure will have a great influence on the refilling. Thus, the onset of the gas should be delayed as long as possible, and should take place with as high speed as possible, see FIGS. 5 and 13.

Thus, a more efficient cardiopulmonary resuscitation is obtained while maintaining physiological safety, which may result in a better outcome for a patient suffering from cardiac arrest.

If the gas supply device and method described above is used together with a mechanical Cardio Pulmonar Resuscitation device of the type LUCAS, mentioned above, the device have essentially five parameters that can be adjusted, viz. the compression depth, the forces of compression and decompression, and the times of compression and decompression.

The compression depth should be about 20% of the vertical distance over the thorax, but can be varied from about 10% to about 30%. A larger compression depth may result in a larger aortic flow, provided that the thorax is properly refilled.

The compression force determines the initiation of phase one, and should be as large as possible to achieve as fast as possible stroke without causing damage of the rib bones or inner organs.

The decompression force determines the initiation of phase four and should be as large as possible to achieve as fast as possible stroke without causing damage.

The compression time is the combined times of phases one, two and three.

The decompression time is the combined times of phases four, five and six.

The compression and decompression times may be equal and each about 0.3 seconds to result in a cycle time of 100 cycles per minute. For example; if there is a tendency that the volume of gas inhaled essentially during phase six becomes larger than the volume of gas exhaled essentially during phase three, the decompression time may be lengthened and the compression time may be shortened, and vice versa.

In addition, the cycle time may be adjusted, for example between 60 to 120 cycles per minute.

Thus, the parameters of the mCPR device and the gas supply device may be combined in different manners for providing a superior end result.

When a mechanical CPR device is used, the timings according to the present invention can be determined based on signals received from the mCPR device.

Figure 8:
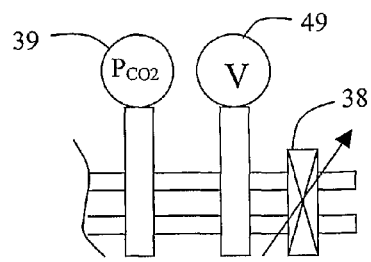
FIG. 8 is a schematic view of an alternative connection of the tracheal tube to the surrounding atmosphere.

In FIG. 8, there is shown an alternative embodiment of the proximal end 25 of the tracheal tube 22. The purpose of the tracheal tube is to generate a constriction that reduces exhalation during phases one and two and reduces inhalation during phases four and five. The constriction should also balance the inhalation, mainly during phase six, and the exhalation, mainly during phase three, so that a balance is achieved in which the lung pressure at the end of phase three and in phases four and five is sufficiently low to allow full replenishment of the thorax.

In addition, the exhalation during phase one and two is reduced by the fact that the supply of gas is on. Thus, the supplied gas has to pass out through the tracheal tube together with the gas from the lungs.

The inhalation volume is mainly controlled by the length of phase six and the flow rate of the gas supplied. The exhalation volume is essentially controlled by the constriction and the time duration of phase three.

In order to achieve a proper balance, the outlet opening of the tracheal tube may be provided with a variable constriction 38, which is controlled so that the desired properties are obtained. The control may take place by a computer 30, which receives as input parameters, the flow rate of gas supplied 35, 37 and the flow rate of gas out through the tracheal tube, measured by a flow meter 49. In addition, a carbon dioxide meter 39 may be arranged for measuring the outflow of carbon dioxide, in order to verify that the patient is properly ventilated. Such a carbon dioxide meter 39 may be a carbon dioxide partial pressure meter, the output signal of which is integrated to indicate total amount of carbon dioxide. In this embodiment, the constriction 38 is adjusted to a relatively permanent value, which is substantially constant over the entire cycle. By making the constriction 38 smaller, the gas supplied during phases six is made larger and the gas removed during phases one, two and three is made smaller. By adjusting the timings, essentially of phases six and three, the gas balance is also influenced upon. Thus, phase three may be made longer in order to lower the thorax/lung pressure during the de-compression phase and promote thorax refilling with blood. Phase three may be made longer on the expense of phase two (shortening of phase two), so that the total cycle time is not amended.

Figure 12:
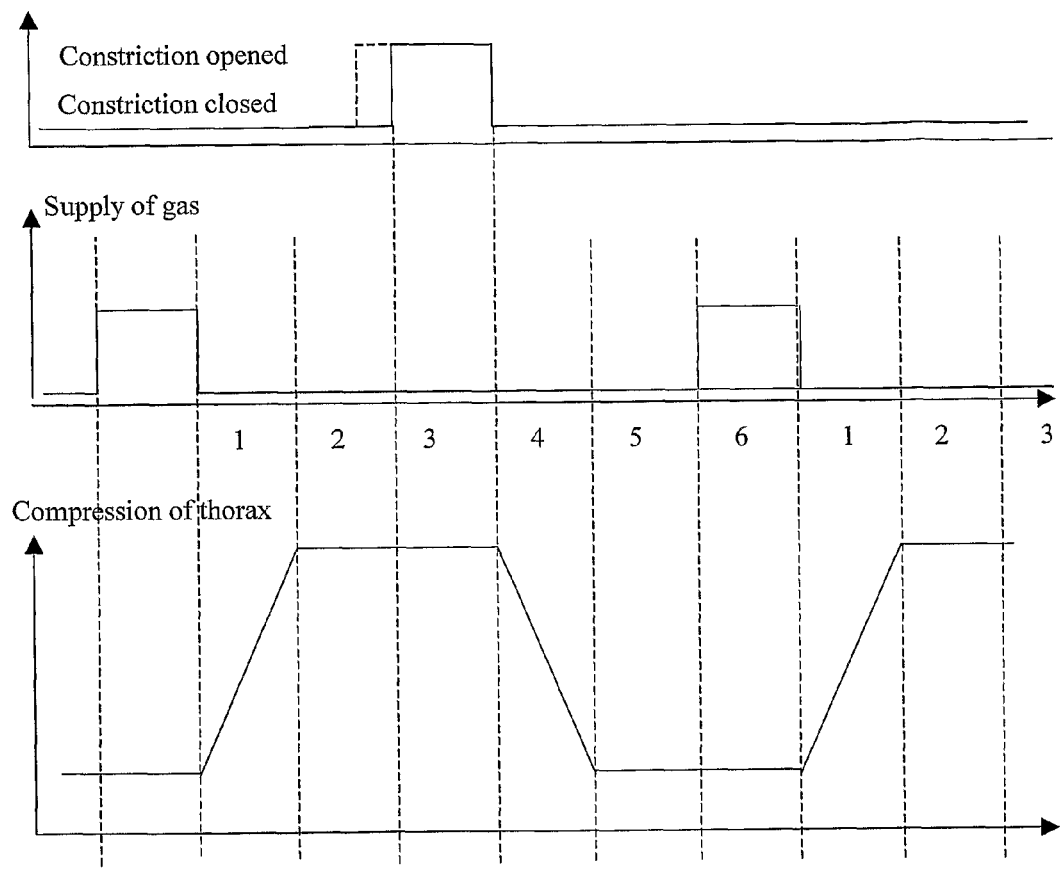
FIG. 12 is a diagram similar to FIG. 9 of the timings of an alternative embodiment.

In an alternative embodiment, the constriction 38 is operated in synchronism with the mCPR. An operation cycle may be as shown in FIG. 12. Before phase one, gas is supplied and the constriction 38 is closed, so that all gas enters the lung. During phases one and two, the gas supply is stopped and the constriction is still closed. Thus, the thorax is isolated from the surrounding atmosphere, and the gas volume will support a high aortic peak pressure during compression. During phase three, the constriction is opened to allow gas to be exhaled until the pressure is lowered. During phases four and five, the constriction is closed to prevent air from being inhaled to the lungs in order to maintain a low pressure in the lungs.

The operation is controlled in the following manner. The gas supply rate and the time of phase six is controlled so that the maximal tracheal pressure is as high as possible but still below 30 mmHg, such as about 25 mmHg. This will ensure a high blood pressure at compression phase. The exhalation of gas during phase three is controlled so that a low pressure close to zero, such as below 5 mmHg, for example below 2 mmHg, is obtained in the right atrium. The exhalation of air is augmented by having as large area as possible in the tracheal tube and by extending the time duration of phase three. Phase three is started as soon as the aortic valve has a tendency to close or slightly earlier. Thus, phase two may be shortened and phase three lengthened. In an embodiment, phase two may be essentially zero, so that phase three follows almost directly after phase one.

Since gas is supplied when the constriction 38 is closed, the gas may in an alternative embodiment be supplied directly to the central channel 23. Thus, no separate gas supply channel 24 is required and only a pressure measurement channel 28 and a balloon and a balloon channel 27 are required. However, in this case, the volume of the central channel 23 is added to the "dead space" of the bronchi. If the central channel 23 is narrow, this may be acceptable.

The exhalation of gas may be augmented by supplying gas when the constriction 38 is open. In this case, the gas should be delivered through an orifice being directed towards the proximal end of the tube. In this way, the gas will flow out through the tube and generate an aspiration of the gas in the bronchi.

Figure 5:
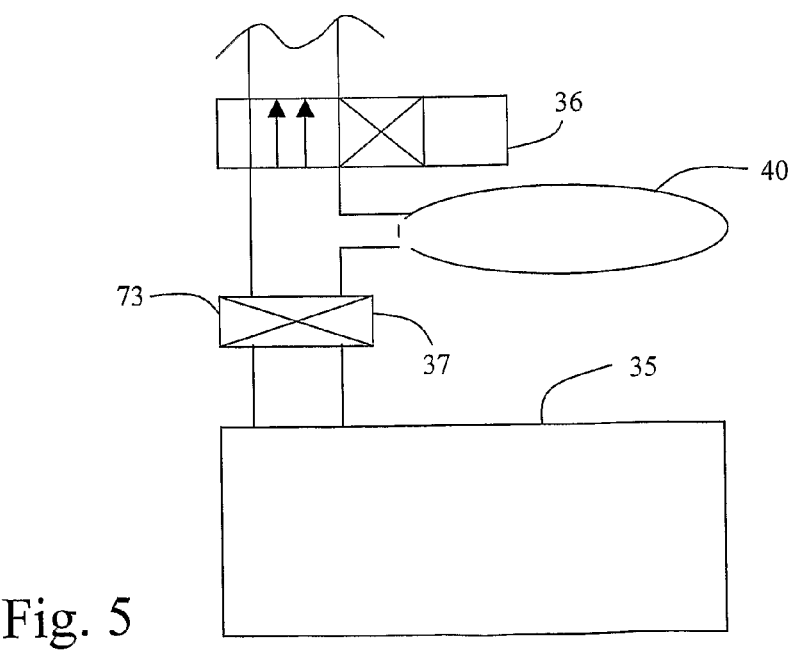
FIG. 5 is a schematic view of an alternative embodiment of the connection of the tracheal tube to a gas supply.
Figure 13:
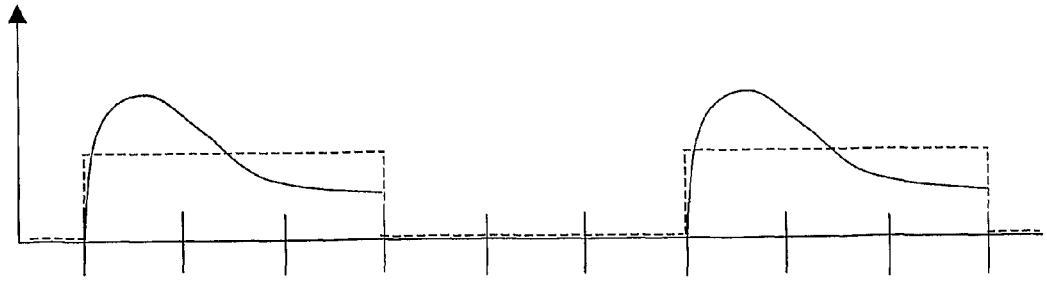
FIG. 13 is a diagram showing supply of gas in the embodiment of FIG. 5.

In FIGS. 9 and 12, the gas supply has been indicated as a square wave. However, the gas supply can be of any shape, such as sinusoidal or with more or less sloping edges. An embodiment having a more sinusoidal supply of gas, at least during phase six, is shown in FIGS. 5 and 13. The gas source 35 is connected to a constant flow valve 37, which is adjusted to the desired average gas flow, such as 15 l/min. The flow valve 37 is connected to the switch valve 36 for opening and closing the supply of gas according to the diagram of FIG. 9. Between flow valve 37 and switch valve 36, there is arranged an accumulator 40, in the nature of a rubber balloon which may expand and contract and develops a predetermined pressure when expanded. During phases three, four and five, when the switch valve 36 is closed, pressure is built up in the accumulator 40. When the switch valve 36 is opened at initiation of phase six, a high pressure prevails in the accumulator 40 and a fast supply of gas is obtained during phase six. Then, during phases one and two, the flow rate is reduced to the flow rate adjusted by the flow valve 37. The gas supply rate is shown in FIG. 13. The exact distribution of the flow rate can be controlled by the resiliency of the accumulator 40 and adjustment of the pressure, which is built up in the accumulator, in combination with the cross-sectional area of the gas supply channel in the tracheal tube.

The timings of the cycle may be controlled by the computer 30 in dependence of the measurement of the pressure meter 34, which measures the gas pressure at the distal end 22 of the tracheal tube.

The computer 30 may be programmed to initiate phase three, i.e. open the constriction 38, when the pressure meter 34 falls below 70% of the maximum gas pressure during phase one.

Moreover, the computer 30 may be programmed to initiate phase six in dependence of the lowest gas pressure during phase five. The computer 30 may be programmed so that phase six is at least a short time period, such as 0.01 seconds. If the pressure of pressure meter 34 in phase five is below 3 mmHg, the time period may be extended in steps until the pressure becomes 3 mmHg, or a desired value.

The above embodiments are intended to make any specific mCPR device as efficient as possible by providing the supply of gas in advance of the compression stroke and/or the removal of gas in advance of the de-compression stroke. However, the physiological outcome of the process is also dependent on the operation of the specific mCPR device, such as the cycle rate and the compression depth. In a mechanical Cardio Pulmonary Resuscitation device of the type LUCAS described above, the compression depth is normally about 20% and the cycle rate is about 100 strokes per minute. The cycle rate may be adjusted to up to 120 strokes per minute or as low as 60 strokes per minute. Such cycle rates will influence upon the timings of the supply and removal of gas. In addition, the compression depth will also influence upon the timings of the supply and removal of gas.

The computer 30 may as well be adjusted to influence upon the mCPR device. Thus, the computer may be arranged to start the decompression phase four when the thorax/lungs have been properly vented, for example when the pressure in the tracheal tube has decreased to a specific value, such as 10% of the maximum value.

The initiation of the compression phase may alternatively be controlled by the computer, for example in dependence of the blood flow in the aorta, which may be measured by an ultrasound-Doppler-probe from outside the body or by the vascular pressures measured by blood pressure meters 71 and 72, see FIG. 1. Thus, the computer may control the cycle time so that maximal aortic blood flow is obtained.

The computer 30 may be arranged to operate the combined gas supply device and the mCPR device as follows, based on the embodiment of FIG. 8 and with an aortic flow meter.

Phase six starts with opening of the gas supply. The gas supply is stopped after a first predetermined time period or after a predetermined volume of gas has been inhaled, and a compression stroke is started. The aortic flow is measured and integrated. The gas pressure of the pressure meter 34 is monitored and when the pressure has decreased to 70% of the maximum reading, the constriction 39 is opened. When the pressure has reached 20% of the maximum reading, a decompression stroke is initiated. The decompression pressure after about 0.1 seconds is measured. The next cycle is adjusted as follows:

If the maximum compression pressure is below 100 mmHg, the gas supply period is increased in order to inhale more gas into the lungs in the next cycle.

If the decompression pressure is above 5 mmHg, the opening time of the constriction is adjusted to a higher value, such as 80% of the maximum reading and/or the initiation of the compression stroke is delayed, for example to 10% of the maximum reading. If this is not sufficient, the gas supply time period is decreased in order to inhale less gas into the lungs in the next cycle.

The cycle time is adjusted so that the aortic flow rate is maximized. This can be done by adjusting the cycle time of the CPR device stepwise in order to find out which cycle time that produces the maximum aortic flow. If the cycle time is too short, the thorax will not have a sufficient time to replenish with blood from vena cava, and if the cycle time is too long, the pump stroke becomes inefficient.

In addition, the time period during decompression, when the aortic valve is closed and there is a coronary perfusion flow, is adjusted so that it is sufficiently long.

In an alternative embodiment, the computer may be controlled in dependence of the measurement of a catheter, which is introduced into an artery, such as the brachial artery, and which measures the blood pressure. The catheter may be inserted further into the artery in order to come closer to the aorta. In addition to the artery pressure, the catheter may measure the amount of oxygen and carbon dioxide in the blood.

The maximum arterial pressure during compression and the minimum arterial pressure during decompression may be used for controlling the time periods mentioned above. Thus, if the maximum pressure is too low, this is an indication that the gas volume supplied should be increased. If the minimum pressure is too high, this is an indication that the removal of gas is insufficient, and the exhalation time period should be extended and/or the gas volume should be decreased. The arterial pressure can be measured by a catheter inserted in the arterial vascular system, for example adjacent the aorta 18 as shown in FIG. 1 by arterial pressure meter 71. In addition, the venous return pressure can be measured by a catheter inserted in the venous vascular system, for example adjacent vena cava 12, as shown by venous pressure meter 72.

In addition, the measurement of the catheter of the oxygen saturation level and the carbon dioxide concentration can be used for providing indications that the supply of oxygen is insufficient and the removal of carbon dioxide is insufficient. If the oxygen saturation level is too low, the supply of gas in the nature of oxygen should be increased. If the removal of carbon dioxide is insufficient, the cycle time may be increased so that a larger gas volume is exchanged for each cycle.

In the description above, the gas supply cycle is off-set before the pulmonary resuscitation cycle, such as 20% before. Since the operation is cyclical, the gas supply cycle can be said to be off-set after the pulmonary cycle, such as 80% after. The two modes are identical.

In an embodiment, the gas supply cycle is defined in relation to the time instance of initiation of a compression stroke of the CPR device. The time between the initiation of two compression strokes is defined as having 100% of time duration. Then, the gas supply is initiated at a time instance of 75% to 98%, which is equivalent to 25% to 2% before the compression stroke. If the cycle time is 0.6 seconds, this definition corresponds to 0.15 to 0.012 seconds before the initiation of the compression stroke, which is equivalent with 0.45 to 0.588 seconds after the initiation of the compression stroke. In this embodiment, the gas supply may be terminated after 10% to 60% of the cycle time. Alternatively, the gas supply is terminated when a predetermined amount of gas has been supplied.

The gas supply cycle may as well be defined in relation to the initiation of a decompression stroke, which is equivalent to when the compression stroke is terminated. In this case, the gas supply is initiated at a time instance of 25% to 48%.

The gas supply is initiated after half the time between the termination of the previous compression stroke and the initiation of the present compression stroke and before the initiation of the present compression stroke.

This embodiment may be controlled by the CPR device in case it is mechanically operated. A signal which initiates a compression stroke and/or a signal which terminates a compression stroke can be used for synchronization purpose as outlined above.

In another case, the above embodiment is controlled by a switch plate 74, see FIG. 2, which is arranged between the sternum of the patient and the pressure pad of the CPR device. When a pressure is exerted on the pressure plate, a switch is activated and when the pressure is removed, the switch is deactivated. This signal may be used for the synchronization. This pressure pad can be used at any type of CPR device, including manual compression of the thorax.

In another embodiment, the gas supply cycle is defined in relation to a reading of a pressure meter, which is connected to the distal end of the gas supply tube. As seen in FIG. 10, the tracheal pressure has a maximum peak and a minimum peak. These peaks are due to the initiation of a compression stroke and the termination of a compression stroke, but are slightly delayed. A device using the pressure meter as synchronization may operate in the following manner. The gas supply is activated and the CPR device is activated. When a first maximum peak is measured, no action is performed until the next peak is measured. Now, the cycle time is determined as the time duration between two consecutive peaks. There may be qualifications on the acceptance of the cycle time, for example that it is between 0.5 and 1.5 seconds, and that the peak is above 15 mmHg etc. Then, the gas supply is operated so that the gas supply is terminated and then activated again at a time instance of 65% to 88%. This is calculated based on a delay of the peak pressure by 10% in relation to the initiation of the compression stroke. The gas supply is terminated 15% to 50% after the activation of the gas supply, or after the delivery of a predetermined amount of gas. When the cycle is established, the exact timings may be finetuned so that a high aortic pressure is obtained at the same time as a proper refilling of the thorax is obtained and a high perfusion pressure is obtained. Since the supply of gas will result in an increase of the pressure meter, such supply of gas must not be interpreted as a peak.

The gas supply may alternatively or additionally be synchronized with a minimum peak reading, which occur some time after the termination of the compression stroke. In some embodiments, this synchronization method may be reliable and produce good results. In this case, the gas supply is initiated at 15% to 38%, provided that the minimum peak is delayed about 10% compared to the termination of the compression stroke. If it is found that the minimum peak and/or the maximum peak are delayed less or more than 10%, the figures should be adapted correspondingly. Such delays should be determined for the specific equipment used. In this embodiment, the gas supply device is completely independent on any CPR device and can be used at any type of pulmonary resuscitation, in which compression of the thorax is performed cyclically.

Another manner to synchronize the gas supply with a thorax compression would be to use a flow meter arranged at the proximal end of the tracheal tube (or adjacent the mouth if only a gas supply tube is used and the exhalation takes place via the trachea), which flow meter measures when the outflow through the tracheal tube is at maximum and/or at minimum. These flow minima or maxima are relatively well synchronized with the corresponding peak pressure readings of the pressure meter, so the same principle applies as indicated above.

The same type of considerations apply for when the supply of gas should be terminated. The termination of the gas supply may be synchronized with the compression cycle in any of the above-mentioned manners. If the gas supply is controlled as to the termination of the gas supply, the gas can be initiated again after Thus, there may be active synchronisation of the initiation of the gas supply or active synchronisation of the termination of the gas supply, or both.

The synchronization can take place based on the initiation of a compression stroke or the termination of the compression stroke, which is equivalent with the initiation of a decompression stroke or both. The synchronization may also take place based on pressure in the trachea or other measureable parameters related to the compression and/or decompression of the thorax or sternum or heart.

A further synchronization method would be to insert a pressure meter in the vascular system, such as the artery system, and use the pressure meter for synchronization purpose, according to the above-mentioned principles.

In the claims, the term "comprises/comprising" does not exclude the presence of other elements or steps. Furthermore, although individually listed, a plurality of means, elements or method steps may be implemented by e.g. a single unit. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

Although the present invention has been described above with reference to specific embodiment, it is not intended to be limited to the specific form set forth herein. Rather, the invention is limited only by the accompanying claims and, other embodiments than the specific above are equally possible within the scope of these appended claims.

The invention claimed is:

1. A method for providing ventilation gas to a patient during a cardiopulmonary resuscitation cycle including a compression stroke and a decompression stroke of a thorax of the patient, comprising:
    arranging a distal end of a gas supply tube in a trachea of the patient;
    supplying said gas to a proximal end of said gas supply tube for delivery of said gas at the distal end of the gas supply tube;
    operating a switch valve for initiating and terminating the supply of gas via the gas supply tube;
    receiving a synchronization signal based on a cardiopulmonary resuscitation cycle;
    synchronizing said operation of the switch valve with said cardiopulmonary resuscitation cycle based on said synchronization signal so that the switch valve operates with the same cycle as the cardiopulmonary resuscitation cycle but off-set in relation to the cardiopulmonary resuscitation cycle; and
    initiating the supply of gas based on the synchronization signal so that the gas supply is initiated between 25% and 2% of the cycle time before the start of a compression stroke.

2. The method as claimed in claim 1, further comprising:
    providing said synchronization signal by means of at least one of:
    a signal emitted by a mechanical cardiopulmonary resuscitation device;
    a pressure switch plate arranged adjacent at the patient and exposed to compression forces during a compression stroke for activation of said switch upon compression of the thorax;
    a gas pressure meter measuring pressure in the gas supplied to the patient;
    a blood pressure meter measuring blood pressure in the vascular system;
    a gas flow meter measuring gas flow out from the lungs to the surroundings.

3. The method as claimed in claim 1, further comprising:
    operating a valve controlling the flow of gas out from the lungs of the patient to the surroundings via a ventilation tube for closing said valve when the supply of gas is activated.

4. The method as claimed in claim 1, further comprising:
    adjusting the supply of gas for providing a predetermined amount of gas per cycle.

5. The method as claimed in claim 1, further comprising:
    receiving as synchronization signal a gas pressure corresponding to the gas pressure in the trachea, and controlling the initiation of the compression stroke as being 2% to 15% of the cycle time before a peak maximum gas pressure or controlling the termination of the compression stroke as being 2% to 15% of the cycle time before a peak minimum gas pressure.

6. A device for providing ventilation gas to a patient during a cardiopulmonary resuscitation cycle including a compression stroke and a decompression stroke of a thorax of the patient, comprising:
    a gas supply tube having a distal end thereof arranging in a trachea of the patient;
    a source of gas for supplying said gas to a proximal end of said gas supply tube for delivery of said gas at the distal end of the gas supply tube;
    a switch valve for initiating and terminating the supply of gas via the gas supply tube; and
    a control device for receiving a synchronization signal based on a cardiopulmonary resuscitation cycle; wherein said device is operated for synchronizing said operation of the switch valve with said cardiopulmonary resuscitation cycle based on said synchronization signal so that the switch valve operates with the same cycle as the cardiopulmonary resuscitation cycle but off-set in relation to the cardiopulmonary resuscitation cycle;
    wherein said control device is operated for initiating the supply of gas based on the synchronization signal so that the gas supply is initiated between 25% and 2% of the cycle time before the start of a compression stroke.

7. The device as claimed in claim 6, further comprising at least one of the following:
    a device for emitting a signal by a mechanical cardiopulmonary resuscitation device;
    a pressure switch plate arranged adjacent at the patient and exposed to compression forces during a compression stroke for activation of said switch upon compression of the thorax;
    a gas pressure meter measuring pressure in the gas supplied to the patient;
    a blood pressure meter measuring blood pressure in a vascular system of the patient;
    a gas flow meter measuring gas flow out from the lungs to the surroundings.

8. The device as claimed in claim 6, further comprising:
    a valve controlling the flow of gas out from the lungs of the patient to the surroundings via a ventilation tube for closing said valve when the supply of gas is activated.

9. A method for providing ventilation gas to a patient during a cardiopulmonary resuscitation cycle including a compression stroke and a decompression stroke of a thorax of the patient, comprising:
    arranging a distal end of a gas supply tube in a trachea of the patient;
    supplying said gas to a proximal end of said gas supply tube for delivery of said gas at the distal end of the gas supply tube;
    operating a switch valve for initiating and terminating the supply of gas via the gas supply tube;
    receiving a synchronization signal based on a cardiopulmonary resuscitation cycle;
    synchronizing said operation of the switch valve with said cardiopulmonary resuscitation cycle based on said synchronization signal so that the switch valve operates with the same cycle as the cardiopulmonary resuscitation cycle but off-set in relation to the cardiopulmonary resuscitation cycle; and terminating the supply of gas based on the synchronization signal so that the gas supply is terminated between 2% and 30% of the cycle time after the start of a compression stroke.

10. The method as claimed in claim 9, further comprising:
providing said synchronization signal by means of at least one of:
a signal emitted by a mechanical cardiopulmonary resuscitation device;
a pressure switch plate arranged adjacent at the patient and exposed to compression forces during a compression stroke for activation of said switch upon compression of the thorax;
a gas pressure meter measuring pressure in the gas supplied to the patient;
a blood pressure meter measuring blood pressure in the vascular system;
a gas flow meter measuring gas flow out from the lungs to the surroundings.

11. The method as claimed in claim 9, further comprising:
operating a valve controlling the flow of gas out from the lungs of the patient to the surroundings via a ventilation tube for closing said valve when the supply of gas is activated.

12. The method as claimed in claim 9, further comprising:
adjusting the supply of gas for providing a predetermined amount of gas per cycle.

13. A method for providing ventilation gas to a patient during a cardiopulmonary resuscitation cycle including a compression stroke and a decompression stroke of a thorax of the patient, comprising:
arranging a distal end of a gas supply tube in a trachea of the patient;
supplying said gas to a proximal end of said gas supply tube for delivery of said gas at the distal end of the gas supply tube;
operating a switch valve for initiating and terminating the supply of gas via the gas supply tube;
receiving a synchronization signal based on a cardiopulmonary resuscitation cycle;
synchronizing said operation of the switch valve with said cardiopulmonary resuscitation cycle based on said synchronization signal so that the switch valve operates with the same cycle as the cardiopulmonary resuscitation cycle but off-set in relation to the cardiopulmonary resuscitation cycle;
and initiating the supply of gas based on the synchronization signal so that the gas supply is initiated between 25% and 48% of the cycle time after the termination of a compression stroke.

14. The method as claimed in claim 13, further comprising:
providing said synchronization signal by means of at least one of:
a signal emitted by a mechanical cardiopulmonary resuscitation device;
a pressure switch plate arranged adjacent at the patient and exposed to compression forces during a compression stroke for activation of said switch upon compression of the thorax;
a gas pressure meter measuring pressure in the gas supplied to the patient;
a blood pressure meter measuring blood pressure in the vascular system;
a gas flow meter measuring gas flow out from the lungs to the surroundings.

15. The method as claimed in claim 13, further comprising:
operating a valve controlling the flow of gas out from the lungs of the patient to the surroundings via a ventilation tube for closing said valve when the supply of gas is activated.

16. The method as claimed in claim 13, further comprising:
adjusting the supply of gas for providing a predetermined amount of gas per cycle.

17. A method for providing ventilation gas to a patient during a cardiopulmonary resuscitation cycle including a compression stroke and a decompression stroke of a thorax of the patient, comprising:
arranging a distal end of a gas supply tube in a trachea of the patient;
supplying said gas to a proximal end of said gas supply tube for delivery of said gas at the distal end of the gas supply tube;
operating a switch valve for initiating and terminating the supply of gas via the gas supply tube;
receiving a synchronization signal based on a cardiopulmonary resuscitation cycle;
synchronizing said operation of the switch valve with said cardiopulmonary resuscitation cycle based on said synchronization signal so that the switch valve operates with the same cycle as the cardiopulmonary resuscitation cycle but off-set in relation to the cardiopulmonary resuscitation cycle; and
terminating the supply of gas based on the synchronization signal so that the gas supply is terminated between 52% and 80% after the termination of a compression stroke.

18. The method as claimed in claim 17, further comprising:
providing said synchronization signal by means of at least one of:
a signal emitted by a mechanical cardiopulmonary resuscitation device;
a pressure switch plate arranged adjacent at the patient and exposed to compression forces during a compression stroke for activation of said switch upon compression of the thorax;
a gas pressure meter measuring pressure in the gas supplied to the patient;
a blood pressure meter measuring blood pressure in the vascular system;
a gas flow meter measuring gas flow out from the lungs to the surroundings.

19. The method as claimed in claim 17, further comprising:
operating a valve controlling the flow of gas out from the lungs of the patient to the surroundings via a ventilation tube for closing said valve when the supply of gas is activated.

20. The method as claimed in claim 17, further comprising:
adjusting the supply of gas for providing a predetermined amount of gas per cycle.

21. A device for providing ventilation gas to a patient during a cardiopulmonary resuscitation cycle including a compression stroke and a decompression stroke of a thorax of the patient, comprising:
a gas supply tube having a distal end thereof arranging in a trachea of the patient;
a source of gas for supplying said gas to a proximal end of said gas supply tube for delivery of said gas at the distal end of the gas supply tube;
a switch valve for initiating and terminating the supply of gas via the gas supply tube;
a control device for receiving a synchronization signal based on a cardiopulmonary resuscitation cycle;
wherein said device is operated for synchronizing said operation of the switch valve with said cardiopulmonary resuscitation cycle based on said synchronization signal so that the switch valve operates with the same cycle as the cardiopulmonary resuscitation cycle but off-set in relation to the cardiopulmonary resuscitation cycle;

wherein said control device is operated for terminating the supply of gas based on the synchronization signal so that the gas supply is terminated between 2% and 30% of the cycle time after the start of a compression stroke.

22. The device as claimed in claim 21, further comprising at least one of the following:
- a device for emitting a signal by a mechanical cardiopulmonary resuscitation device;
- a pressure switch plate arranged adjacent at the patient and exposed to compression forces during a compression stroke for activation of said switch upon compression of the thorax;
- a gas pressure meter measuring pressure in the gas supplied to the patient;
- a blood pressure meter measuring blood pressure in a vascular system of the patient;
- a gas flow meter measuring gas flow out from the lungs to the surroundings.

23. The device as claimed in claim 21, further comprising:
a valve controlling the flow of gas out from the lungs of the patient to the surroundings via a ventilation tube for closing said valve when the supply of gas is activated.

24. A device for providing ventilation gas to a patient during a cardiopulmonary resuscitation cycle including a compression stroke and a decompression stroke of a thorax of the patient, comprising:
- a gas supply tube having a distal end thereof arranging in a trachea of the patient;
- a source of gas for supplying said gas to a proximal end of said gas supply tube for delivery of said gas at the distal end of the gas supply tube;
- a switch valve for initiating and terminating the supply of gas via the gas supply tube;
- a control device for receiving a synchronization signal based on a cardiopulmonary resuscitation cycle; wherein said device is operated for synchronizing said operation of the switch valve with said cardiopulmonary resuscitation cycle based on said synchronization signal so that the switch valve operates with the same cycle as the cardiopulmonary resuscitation cycle but off-set in relation to the cardiopulmonary resuscitation cycle;
- wherein said control device is operated for initiating the supply of gas based on the synchronization signal so that the gas supply is initiated between 25% and 48% of the cycle time after the termination of a compression stroke.

25. The device as claimed in claim 24, further comprising at least one of the following:
- a device for emitting a signal by a mechanical cardiopulmonary resuscitation device;
- a pressure switch plate arranged adjacent at the patient and exposed to compression forces during a compression stroke for activation of said switch upon compression of the thorax;
- a gas pressure meter measuring pressure in the gas supplied to the patient;
- a blood pressure meter measuring blood pressure in a vascular system of the patient;
- a gas flow meter measuring gas flow out from the lungs to the surroundings.

26. The device as claimed in claim 24, further comprising:
a valve controlling the flow of gas out from the lungs of the patient to the surroundings via a ventilation tube for closing said valve when the supply of gas is activated.

27. A device for providing ventilation gas to a patient during a cardiopulmonary resuscitation cycle including a compression stroke and a decompression stroke of a thorax of the patient, comprising:
- a gas supply tube having a distal end thereof arranging in a trachea of the patient;
- a source of gas for supplying said gas to a proximal end of said gas supply tube for delivery of said gas at the distal end of the gas supply tube;
- a switch valve for initiating and terminating the supply of gas via the gas supply tube;
- a control device for receiving a synchronization signal based on a cardiopulmonary resuscitation cycle; wherein said device is operated for synchronizing said operation of the switch valve with said cardiopulmonary resuscitation cycle based on said synchronization signal so that the switch valve operates with the same cycle as the cardiopulmonary resuscitation cycle but off-set in relation to the cardiopulmonary resuscitation cycle;
- wherein said control device is operated for terminating the supply of gas based on the synchronization signal so that the gas supply is terminated between 52% and 80% after the termination of a compression stroke.

28. The device as claimed in claim 27, further comprising at least one of the following:
- a device for emitting a signal by a mechanical cardiopulmonary resuscitation device;
- a pressure switch plate arranged adjacent at the patient and exposed to compression forces during a compression stroke for activation of said switch upon compression of the thorax;
- a gas pressure meter measuring pressure in the gas supplied to the patient;
- a blood pressure meter measuring blood pressure in a vascular system of the patient;
- a gas flow meter measuring gas flow out from the lungs to the surroundings.

29. The device as claimed in claim 27, further comprising:
a valve controlling the flow of gas out from the lungs of the patient to the surroundings via a ventilation tube for closing said valve when the supply of gas is activated.

* * * * *